(12) United States Patent
Topolkaraev et al.

(10) Patent No.: US 6,627,673 B2
(45) Date of Patent: Sep. 30, 2003

(54) METHODS OF MAKING HUMIDITY ACTIVATED MATERIALS HAVING SHAPE-MEMORY

(75) Inventors: Vasily A. Topolkaraev, Appleton, WI (US); Dave A. Soerens, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/911,987

(22) Filed: Jul. 24, 2001

(65) Prior Publication Data

US 2003/0060530 A1 Mar. 27, 2003

(51) Int. Cl.$^7$ .................................................. C08J 3/28
(52) U.S. Cl. ..................... 522/111; 522/112; 522/149; 522/150; 522/151; 522/152; 522/153; 522/154; 522/155; 522/156; 522/157; 522/158; 522/159; 522/161; 522/906; 525/50; 525/55; 525/58; 525/123; 525/66; 264/232; 264/485; 264/488; 524/921
(58) Field of Search ............................. 525/50, 55, 58, 525/123, 66, 59, 63, 64, 65, 69, 71, 78, 79, 80, 83, 88, 89, 90, 94; 522/109, 84, 110, 111, 112, 149–167, 906; 264/232, 485, 488; 524/921; 252/194

(56) References Cited

U.S. PATENT DOCUMENTS

| | | | |
|---|---|---|---|
| RE22,038 E | | 2/1942 | Milas |
| 2,509,674 A | | 5/1950 | Cohen |
| 2,608,334 A | * | 8/1952 | Knocke et al. ............. 264/230 |
| 2,885,105 A | * | 5/1959 | Heyl et al. ................... 156/86 |
| 3,079,921 A | * | 3/1963 | Brecht et al. ............... 604/375 |
| 3,560,292 A | | 2/1971 | Butter |
| 3,616,770 A | | 11/1971 | Blyther et al. |
| 3,819,401 A | | 6/1974 | Massengale et al. |
| 3,834,389 A | * | 9/1974 | Dulle ......................... 604/369 |
| 3,860,003 A | | 1/1975 | Buell |
| 3,912,565 A | | 10/1975 | Koch et al. |
| RE28,688 E | | 1/1976 | Cook |
| 3,995,636 A | * | 12/1976 | Murray et al. .............. 604/286 |
| 4,096,230 A | * | 6/1978 | Haerr ......................... 264/320 |
| 4,159,719 A | * | 7/1979 | Haerr ......................... 128/865 |
| 4,239,578 A | | 12/1980 | Gore |
| 4,261,782 A | | 4/1981 | Teed |
| 4,309,236 A | | 1/1982 | Teed |
| 4,324,245 A | | 4/1982 | Mesek et al. |
| 4,352,355 A | | 10/1982 | Mesek et al. |
| 4,675,139 A | | 6/1987 | Kehe et al. |
| 4,681,580 A | | 7/1987 | Reising et al. |
| 4,710,189 A | | 12/1987 | Lash |
| 4,820,590 A | | 4/1989 | Hodgson, Jr. et al. |
| 4,839,450 A | * | 6/1989 | Fanta et al. ........... 260/DIG. 43 |
| 5,033,950 A | * | 7/1991 | Will ............................ 249/134 |
| 5,096,206 A | * | 3/1992 | Andre et al. ................. 277/314 |
| 5,112,903 A | * | 5/1992 | Sakakibara et al. ........ 525/54.2 |
| 5,429,856 A | | 7/1995 | Krueger et al. |
| 5,439,966 A | | 8/1995 | Graham et al. |
| 5,445,604 A | * | 8/1995 | Lang ............................ 602/47 |
| 5,474,065 A | | 12/1995 | Meathrel et al. |
| 5,513,660 A | | 5/1996 | Simon et al. |
| 5,536,921 A | | 7/1996 | Hedrick et al. |
| 5,609,817 A | * | 3/1997 | Patil et al. ................. 264/211.11 |
| 5,634,936 A | | 6/1997 | Linden et al. |
| 5,665,477 A | | 9/1997 | Meathrel et al. |
| 5,752,525 A | | 5/1998 | Simon et al. |
| 5,756,651 A | | 5/1998 | Chen et al. |
| 5,782,787 A | * | 7/1998 | Webster ....................... 602/43 |
| 5,910,357 A | | 6/1999 | Hachisuka et al. |
| 5,916,203 A | | 6/1999 | Brandon et al. |
| 5,950,325 A | | 9/1999 | Mehdizadeh et al. |
| 6,005,041 A | | 12/1999 | Cook |
| 6,034,149 A | | 3/2000 | Bleys et al. |
| 6,080,461 A | | 6/2000 | Wozniak et al. |
| 6,096,012 A | | 8/2000 | Bogert et al. |
| 6,096,668 A | * | 8/2000 | Abuto et al. ................. 348/578 |

FOREIGN PATENT DOCUMENTS

| | | | |
|---|---|---|---|
| EP | 1000958 | | 5/2000 |
| EP | 1033145 | | 9/2000 |
| GB | 2081721 | * | 2/1982 |
| GB | 2160473 A | | 12/1985 |
| GB | 2 296 512 A | | 7/1996 |
| JP | 4-239035 | * | 8/1992 |
| JP | 5-177708 | * | 7/1993 |
| JP | 5-177709 | * | 7/1993 |
| JP | 8-132526 | * | 5/1996 |

* cited by examiner

Primary Examiner—James J. Seidleck
Assistant Examiner—Sanza L. McClendon
(74) Attorney, Agent, or Firm—Kilpatrick Stockton LLP

(57) ABSTRACT

The present invention relates to shape deformable materials, which are capable of (1) being deformed, (2) storing an amount of shape deformation, and (3) recovering at least a portion of the shape deformation when exposed to a humid environment. The shape deformable materials can advantageously be in the form of films, fibers, filaments, strands, nonwovens, and pre-molded elements. The shape deformable materials of the present invention may be used to form products, which are both disposable and reusable. More specifically, the shape deformable materials of the present invention may be used to produce products such as disposable diapers, training pants, incontinence products, and feminine care products.

29 Claims, 2 Drawing Sheets

METHODS OF MAKING HUMIDITY ACTIVATED MATERIALS HAVING SHAPE-MEMORY

FIELD OF THE INVENTION

The present invention relates to methods of making materials having a shape memory which is activated when the products are exposed to high humidity or moist environments.

BACKGROUND OF THE INVENTION

Disposable absorbent products are typically subjected to one or more liquid insults, such as of water, urine, menses, or blood, during use. As such, the outer cover backsheet materials of the disposable absorbent products are typically made of liquid-insoluble and liquid impermeable materials, such as polypropylene films, that exhibit a sufficient strength and handling capability so that the disposable absorbent product retains its integrity during use by a wearer and does not allow leakage of the liquid insulting the product.

Although current disposable and reusable garments have been generally accepted by the public, these products still have the need of improvement in specific areas. For example, many absorbent products have a tendency to lose their shape or become uncomfortable to wear after the products are subjected to liquid insults and in-use conditions of high humidity and body temperature. Such changes in shape often result in ill fitting absorbent products and/or leakage.

Typically elastomeric materials are incorporated into disposable and reusable products to improve the fit of the products and prevent leakage during use. These elastomeric materials may be attached to the disposable product by several methods. At one time, elastic was applied to the substrate by sewing. (See U.S. Pat. No. 3,616,770 to Blyther et al.; and U.S. Pat. No. 2,509,674 and U.S. Pat. No. RE 22,038 to Cohen). A newer method for attaching elastomeric material to a substrate is by use of an adhesive. (See U.S. Pat. No. 3,860,003 to Buell.) Welding, such as sonic welding, has also been used to attach elastomeric material to a disposable product. (U.S. Pat. No. 3,560,292 to Butter). Laminates having an elastomeric layer and a co-extensive skin layer have also been used. (U.S. Pat. No. 5,429,856 to Kruger et al.).

However, these methods of attachment present several problems. First is the problem of how to keep the elastic in a stretched condition while applying the elastic to the substrate. Another problem is that attachment of a ribbon of elastomeric material will concentrate the elastomeric force in a relatively narrow line. This may cause the elastic to pinch and irritate the wearer's skin. (See U.S. Pat. Nos. 3,860,003; 4,352,355; and 4,324,245 to Musek et al.; U.S. Pat. No. 4,239,578 to Gore; and U.S. Pat. Nos. 4,309,236 and 4,261,782 to Teed.) Other disadvantages of conventional attachment methods include speed, ease of manufacture, and cost. More importantly, difficulties may be encountered in maintaining a uniform tension on the elastic layer during its attachment to the substrate and also in handling the shirred article once the elastic layer is relaxed.

Heat-responsive elastomeric films overcome some of these detriments. Heat-responsive elastomers exist in two forms: a thermally-stable and a thermally-unstable form. The thermally-unstable form is created by stretching the material while heating near its crystalline or second phase transition temperature, followed by a rapid quenching to freeze it in the thermally-unstable, extended form. The elastomeric film can then be applied to a disposable product, for example a diaper, and heated to shirr or gather the elastomeric material, thereby producing a thermally-stable form of the elastomeric material. Examples of heat-responsive elastomeric films are disclosed in U.S. Pat. No. 4,681,580 to Reising et al., U.S. Pat. No. 4,710,189 to Lash, U.S. Pat. No. 3,819,401 to Massengale et al., U.S. Pat. No. 3,912,565 to Koch et al., and U.S. Pat. No. RE 28,688 to Cook.

These polymers have several disadvantages. The first of these disadvantages involves the temperature to which the elastomeric material must be heated to stretch the material to its thermally-unstable form. This temperature is an inherent property of the elastomeric material. Therefore, the disposable product is often difficult to engineer because temperatures useful for the production of the overall product may not be compatible with the temperature necessary to release the thermally-unstable form of the elastomer. Frequently, this temperature is rather high and can be detrimental to the adhesive material used to attach the various product layers. Another drawback to the use of heat-responsive elastomers is that they can constrain the manufacturing process, rendering it inflexible to lot variations, market availability, cost of raw materials, and customer demands.

U.S. Pat. No. 4,820,590 to Hodgkin et al. describes an elastomeric blend of three components to reduce the temperature required for the material to resume its heat stable form. Additionally, GB Patent 2,160,473 to Matray et al. proposes an elastomer which will shrink at an elevated temperature, for example at or above 170° F. The advantageous features of these materials, compared to the heat-shrinkable materials discussed above, is that it does not require preheating during the stretching operation, but rather can be stretched at ambient temperatures by a differential speed roll process or by "cold rolling."

Problems with use of these elastomers include difficulties inherent in applying a stretched elastic member to a flexible substrate such as a disposable diaper. Although some of the elastomers proposed have the advantage that they can be applied at ambient conditions in a highly stretched, unstable form, subsequent, often extreme, heating is required to release the thermally-unstable form to a contracted thermally-stable form. The temperature of this heat release is generally inflexible since it is determined at the molecular level of the elastomer. Thus, selection of materials for the disposable product which are compatible with this heating step is required.

Further, when individual heat activated elastic materials are used, the heat activation is generally accomplished by passing the garments through a heated air duct for a period of time. Since thermal heating must be transferred from an outer surface of the garment to inner portions of the garment, distribution of the activation means (i.e., thermal heat) throughout the garment takes considerable amounts of time and energy, resulting in an inefficient activation process. As a result, such heating processes can consume vast amounts of energy and undesirably result in slower manufacturing speeds.

What is needed in the art is a method of activating a shape deformation of a material without using an inefficient thermal heating activation process. What is also needed in the art is a method of activating a shape deformation of a material without substantially increasing the temperature of the material. Furthermore, there is a need for new materials that may be used in disposable absorbent products that generally retain their integrity during use, are easily disposed of, and have the ability to change to a desired shape and/or texture during in-use conditions. For example, upon exposure to a high humidity environment, the disposable product may transform to a desired product configuration which will guard against leakage.

SUMMARY OF THE INVENTION

The present invention addresses some of the difficulties and problems discussed above by providing a method of making a humidity responsive material having an amount of locked-in shape deformation. The method includes forming a latent deformation in the humidity responsive material. The material is capable of being deformed in at least one spatial dimension when exposed to one or more external forces, is capable of maintaining a degree of deformation in at least one spatial dimension once the external force is removed, and is capable of exhibiting a change, or percent recovery, in at least one spatial dimension when subjected to a humid or moist environment. The humid or moist environment may be created by in-use conditions of absorbent products.

More particularly, the latent deformation is formed by stretching the humidity responsive material. The stretched material possesses a draw or stretch ratio of at least 1.5 in one or more directions. In addition, the humidity responsive material is heated during stretching to a temperature of not more than about 120° C.

Still more particularly, the humidity responsive material contains at least one shape deformable matrix material. The shape deformable matrix material may contain an elastomeric polymer and a non-elastomeric polymer, such as a moisture absorbing polymer. The humidity responsive material of the present invention finds applicability in a number of products, including products containing a gatherable or elastic part.

The present invention is further directed to a method of causing the shape deformation of materials having a desired amount of locked-in shape deformation. The method includes subjecting the material to a humid environment having a relative humidity of at least 50%. The method may be used to cause the shape deformation of the above-described material itself or a product containing the above-described material.

The present invention is further directed to a method of building shape deformable polymers in an effort to optimize the interaction of the shape deformable polymer with a selected level of humidity. By adjusting the chemical structure of the shape deformable polymer, one can tailor a specific shape deformable polymer in such a way as to maximize the interaction of the shape deformable polymer with a selected humidity level.

These and other features and advantages of the present invention will become apparent after a review of the following detailed description of the disclosed embodiments and the appended claims.

BRIEF DESCRIPTION OF THE DRAWINGS

The present invention is further described by the accompanying drawings, in which.

DETAILED DESCRIPTION OF THE INVENTION

Figure 1:
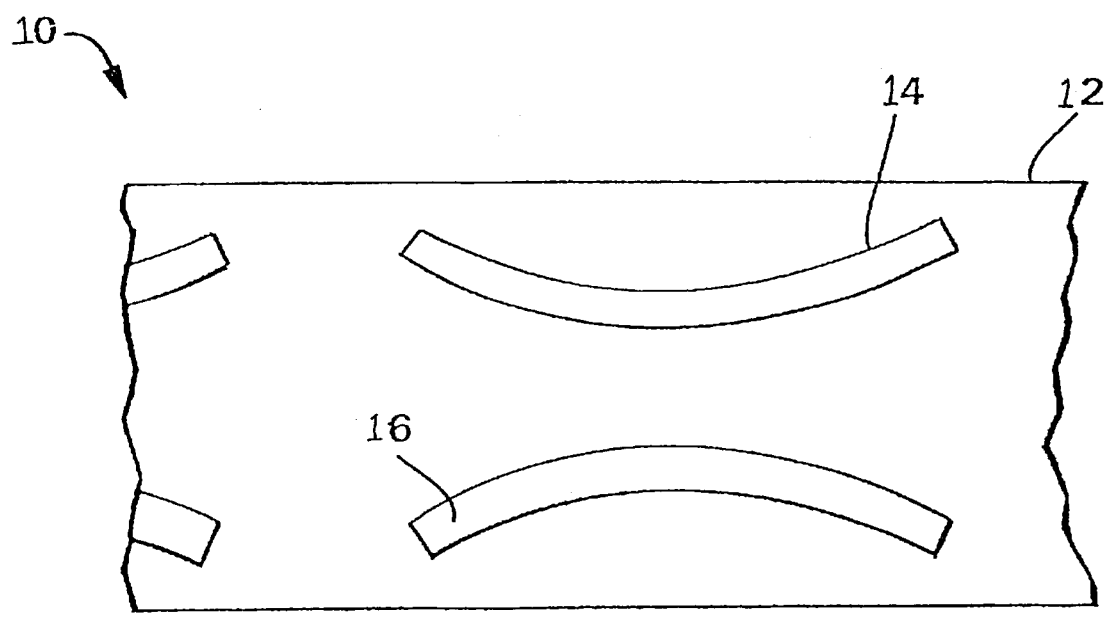
FIG. 1 representatively shows a top plan view of a composite material according to one embodiment of the present invention.

The present invention addresses some of the difficulties and problems discussed above by the discovery of materials which are capable of exhibiting a shape deformation when exposed to humidity, and methods of using the same. These materials exhibit a change in at least one spatial dimension when subjected to high humidity or a moist environment. Unlike known materials and methods, the materials and methods of the present invention maximize the amount of "locked-in" shape deformation within the material, as well as, maximize the percent change in one or more spatial dimensions of the material. Further, unlike previous recovery methods which involve a heating step, the present invention is directed to a method of causing a change in one or more spatial dimensions of the material without a substantial change in the temperature of the material. The recovery method of the present invention instead includes subjecting the material to a level of humidity or moisture sufficient to cause a desired change in one or more spatial dimensions without a substantial change in the temperature of the material. The materials and methods of the present invention find applicability in a number of products and processes.

One method of measuring the change in one or more spatial dimensions of a material is given by the equation below:

$$\% R = \frac{(\delta_i - \delta_f)}{\delta_i} \times 100$$

wherein:

% R represents the percent change, or the percent recovery, of one spatial dimension of the material;

$\delta_i$ represents the dimension prior to subjection to humidity activation; and $\delta_f$ represents the dimension after subjection to the humidity activation.

The above equation may be used to determine the percent recovery of one or more spatial dimensions of the shape deformable material of the present invention. Further, the above equation may be used on any material capable of experiencing a change in a spatial dimension. Suitable materials having a shape deformation and a desired percent recovery are given below.

Shape Deformable Material Components

The present invention is directed to shape deformable materials, which exhibit a change in at least one spatial dimension when subjected to a humid environment. Suitable materials include any material or blend of materials, which has the following properties: (1) is capable of being deformed in at least one spatial dimension when exposed to one or more external forces, (2) is capable of maintaining a degree of deformation in at least one spatial dimension once the external force is removed, and (3) is capable of exhibiting a change, or percent recovery, in at least one spatial dimension when subjected to a humid environment.

The shape deformable materials of the present invention are "humidity softenable". As used herein, the term "humidity softenable" is meant to refer to a material which when placed in a humid environment can dramatically reduce its stiffness and modulus, at least about 20%, and/or relax as a result of moisture absorption from the environment. Preferably, when subjected to a humid environment, the shape deformable material has a reduction in stiffness and modulus of at least about 30%, and more preferably at least about 50%. The term "modulus" as used herein, is meant to refer to the elastic tensile modulus calculated according to ASTM Standard D882-95a, which is incorporated herein by reference. Generally, the elastic tensile modulus is calculated by dividing the tensile stress of the polymer by the corresponding strain.

The shape deformable materials of the present invention may contain one or more of the following classes of components:

Shape Deformable Matrix Materials

The shape deformable materials of the present invention contain at least one shape deformable matrix material. As used herein, the term "shape deformable matrix material" is used to describe a material having the above-mentioned properties, and is also capable of encompassing one or more filler materials. Suitable shape deformable matrix materials include, but are not limited to polymers.

In one embodiment of the present invention, the shape deformable matrix material contains at least one polymer, and more preferably two polymers. Suitable polymers include, but are not limited to, segmented block copolymers comprising one or more hard segments and one or more soft segments; polyester-based thermoplastic polyurethanes; polyether-based polyurethanes; polyethylene oxide; poly (ether ester) block copolymers; polyamides; poly(amide esters); poly(ether amide) copolymers; polyvinyl alcohol; polyvinyl pyrolidone; polyvinyl pyridine; polyacrylic acid; polymethacrylic acid; polyaspartic acid; maleic anhydride methylvinyl ether copolymers of varying degrees of hydrolysis; polyvinyl methyl ether copolymers of polyacrylic acid and polyacrylic esters; and mixtures thereof. Desirably, the shape deformable matrix material contains a segmented block copolymer comprising one or more hard segments and one or more soft segments, where either the soft segment, the hard segment, or both contain functional groups or receptor sites that are responsive to humidity.

As used herein, the phrase "responsive to humidity" is used to describe functional groups and/or receptor sites within a polymer, which, when exposed to a humid environment enables a desired amount of shape recovery of a shape deformed polymer. As used herein, the phrase "humid environment" or "humidity" refers to an environment having at least 50% relative humidity. Suitable functional groups and/or receptor sites include, but are not limited to, functional groups such as urea, amide, nitro, nitrile, ester, ether, hydroxyl, ethylene oxide, and amine groups; carboxylic acid salts, and sulfonic acid salts; ionic groups, such as sodium, zinc, and potassium; and receptor sites having an unbalanced charge distribution formed from one or more of the above groups. Desirably, the functional groups contain one or more functional groups having a high dipole moment (i.e., greater than about 1.5 Debye) such as urea, amide, nitro, and nitrile groups.

More desirably, the segmented block copolymer is an elastomer. Suitable shape deformable elastomers for use in the present invention include, but are not limited to, polyurethane elastomers, polyether elastomers, poly(ether amide) elastomers, polyether polyester elastomers, polyamide-based elastomers, thermoplastic polyurethanes, poly(ether-amide) block copolymers, thermoplastic rubbers such as uncrosslinked polyolefins, styrene-butadiene copolymers, silicon rubbers, synthetic rubbers such as nitrile rubber, butyl rubber, ethylene-vinyl acetate copolymer, styrene isoprene copolymers, styrene ethylene butylene copolymers and mixtures of thereof. Some non-elastomeric polymers may be used. These polymers can provide some degree of recovery when exposed to humidity. Examples of non-elastomeric polymers useful in the present invention include, but are not limited to, polyethylene oxide, copolymers of polylactic acid, blends and mixtures thereof.

In one embodiment of the present invention, the shape deformable matrix material contains a polyurethane. Suitable polyurethanes for use in the present invention include, but are not limited to, polyester-based aromatic polyurethanes, polyester-based aliphatic polyurethanes, polyether-based aliphatic and aromatic polyurethanes, and blends and mixtures of these polyurethanes. Such polyurethanes may be obtained, for example, from Huntsman Polyurethanes (Chicago, Ill.). Examples of specific polyurethanes, which can be used in the present invention include, but are not limited to, MORTHANE® PS370-200, MORTHANE® PS79-200, MORTHANE® PN3429, and MORTHANE® PE90-100. Other thermoplastic polyurethanes applicable for the present invention can be obtained from BF Goodrich Performance Materials under the trade name ESTANE® polyurethanes.

In a further embodiment of the present invention, the shape deformable matrix material includes a poly(ether amide) elastomer. Poly(ether amide) elastomers, which may be used in the present invention, may be obtained, for example, from Elf Atochem North America, Inc. (Philadelphia, Pa.). Examples of such poly(ether amide) elastomers include, but are not limited to, PEBAX® 2533, PEBAX® 3533, and PEBAX® 4033.

Polyurethane elastomers and poly(ether amide) elastomers are particularly useful as the shape deformable matrix material in the present invention because they structurally consist of soft and hard segments, which contain groups having high dipole moments (i.e., isocyanate, amide, and ester groups) which are sensitive to humidity. In addition, due to the high polarity of the high dipole moments, these elastomers are easily blended or combined with a humidity sensitive component. For example, the humidity sensitive component may be blended with the elastomer or otherwise incorporated into the molecular structure of the elastomer. The hard segments in these elastomers typically act as physical cross-linking points for the soft segments, enabling an elastomeric performance. Both hard and soft segments may contribute to the shape deformation during a number of pre-activation treatments described below, such as stretching, which provides "locked-in" shape deformation, which may be recoverable by exposure to a humid environment.

In still another embodiment of the present invention, the shape deformable matrix material includes a blend of an elastomeric polymer and a non-elastomeric polymer. These blends may either be co-extruded together, or may be formed into multi- or micro-layer structures. Alternatively, the multi-layer or micro-layer structure may be formed from separate layers of the elastomeric polymer and non-elastomeric polymer. These layers may or may not be alternating layers. Blends are advantageous since blending or multi-layering/micro-layering of a shape deformation elastomer with another non-elastomeric shape deformation polymer can improve latent deformation properties, especially at lower stretching temperatures, and can significantly increase recoverable deformation as a result of activation by humidity.

For example, the shape deformable matrix material may contain an elastomeric polymer, and a non-elastomeric polymer such as a moisture absorbing polymer, which can soften and relax as a result of moisture absorption. The elastomeric polymer provides force for the dimensional change when the moisture absorbing polymer is softened and relaxed. The moisture absorbing polymer is "humidity softenable". The moisture absorbing polymer can dramatically reduce its stiffness and modulus, at least about 20%, and/or relax as a result of moisture absorption from the environment. Preferably, when subjected to a humid environment, the moisture absorbing polymer has a reduction in stiffness and modulus of at least about 30%, and more preferably at least about 50%. Elevated temperatures, including exposure to body temperature, can facilitate moisture absorption. In addition, the rate of moisture absorption can vary which can provide a control over time-dependent response.

The blend should contain an amount of moisture absorbing polymer which will be effective in achieving the desired humidity activated shape. The humidity softenable polymer will be present in the shape deformable matrix material in an amount from greater than 0 to less than 100 weight percent. Preferably, the shape deformable matrix material contains from about 5% to about 90% by weight moisture absorbing polymer. More preferably, the material contains from about 10% to about 60% by weight moisture absorbing polymer. Examples of suitable moisture absorbing polymers include, but are not limited to polyethylene oxide, polyethylene glycol, polyvinyl alcohol, polyvinyl pyrolidone, polyvinyl pyridine, or mixtures thereof. Preferably, the moisture absorbing polymer is polyethylene oxide. The moisture absorbing polymer should have an ability to be stretched or otherwise plastically deformed to lock in a deformation and/or shape change which can be released later when the polymer is softened in a humid environment.

The elastomeric polymer present in the blend should have the ability to be stretched or deformed from its original length and to retract upon the release of the stretching or deformation force. The elastomeric polymer may have permeability for water vapor which can facilitate moisture absorption by the humidity-softenable polymer. The elastomeric polymer component of the shape deformable matrix material should be present in an amount which is effective to achieve the desired dimensional change properties. The elastomeric polymer will be present in the shape deformable matrix material in an amount from greater than 0 to less than 100 weight percent. Preferably, the shape deformable matrix material contains from about 10% to about 95% by weight elastomeric polymer. More preferably, the material contains from about 50% to about 70% by weight elastomeric material. Examples of suitable elastomeric polymers include, but are not limited to thermoplastic polyurethanes, poly(etheramide) block copolymers, thermoplastic rubbers such as uncrosslinked polyolefins, styrene-butadiene copolymers, silicon rubbers, synthetic rubbers such as nitrile rubber, styrene isoprene copolymers, styrene ethylene butylene copolymers, butyl rubber, nylon copolymers, spandex fibers comprising segmented polyurethane, ethylene-vinyl acetate copolymer or mixtures thereof. Preferably, the elastomeric polymer is polyurethane.

The moisture absorbing polymer and elastomeric polymer may be combined by any method known in the art. For example, the polymers may be mixed, blended, laminated, coextruded, microlayered, or fiberized in a core-shell structure or in a side by side structure. Depending on the ratio of the elastomeric polymer and the moisture absorbing polymer, the blend can demonstrate elastomeric properties or the properties of a ductile thermoplastic polymer.

Non-Activatable Materials

As used herein, the term "non-activatable materials" is used to describe any material, which lacks one or more of the three properties mentioned above when describing suitable shape deformable materials. Suitable non-activatable additional materials include, but are not limited to, non-elastomeric polymers, tackifiers, anti-blocking agents, fillers, antioxidants, UV stabilizers, polyolefin-based polymers and other cost-saving additives that may be added or blended to add beneficial properties.

The amount of non-activatable material blended with the above-mentioned shape deformable polymers may vary as long as the resulting blend possesses a desired amount of shape deformation properties. The blend may contain from about 40 to 99.5 weight percent of shape deformable polymer and from about 60 to 0.5 weight percent of additional non-activatable materials. Desirably, the blend contains from about 60 to 99.5 weight percent of shape deformable polymer and from about 40 to 0.5 weight percent of additional materials. More desirably, the blend contains from about 80 to 99.5 weight percent of shape deformable polymer and from about 20 to 0.5 weight percent of additional non-activatable materials.

Configuration of Shape Deformable Materials

The shape deformation materials of the present invention may possess a variety of shapes and sizes. The shape deformation materials of the present invention may be in the form of blends, films, multi-layered or micro-layered films, laminates, filaments, fabrics, foams, nonwovens or any other three-dimensional form. In many embodiments, particularly for use in personal care products, a preferred substrate is nonwoven material. As used herein, the term "nonwoven material" refers to material that has a structure of individual fibers or filaments randomly arranged in a mat-like fashion. Nonwoven material may be made from a variety of processes, including, but not limited to spunbond processes, meltblown processes, air-laid processes, wet-laid processes, hydroentangling processes, staple fiber carding and bonding, and solution spinning.

The shape deformation material may be formed by any method known to those of ordinary skill in the art including, but not limited to, extrusion, coating, foaming, etc. In addition, the shape deformation material may be formed by blending or combining a material with a humidity responsive component. Alternatively, a humidity responsive component may be incorporated into the molecular structure of a compound to produce the shape deformation material. There is no limitation on the size of the shape deformation material; however, the amount of shape deformation and the percent recovery of the shape deformation material may be limited if the size of the material is too great.

In an alternative embodiment, materials that include a blend of two shape-deformable polymers or a multi- or micro-layer structure having two shape-deformable polymers demonstrate that blending or multi-layering/microlayering of a shape deformation elastomer with another non-elastomeric shape deformation polymer can improve latent deformation properties, especially at lower stretching temperatures, and can significantly increase recoverable deformation as a result of activation by humidity.

Regardless of the size and shape of the shape deformation material, the shape deformation material of the present invention exhibits a change in at least one spatial dimension when subjected to a humid environment. Typically, the shape deformation material of the present invention exhibits a change in one, two, or three dimensions. For example, when the shape deformation material is in the form of a fiber, the shape deformation material exhibits a change in the fiber length and/or fiber diameter. When the shape deformation material is in the form of a film, the shape deformation material exhibits a change in the film length and/or film width and film thickness. A percent recovery may be measured for each of the dimensions of the shape deformation material.

As can be seen by the above equation, in order to maximize the percent recovery of a given dimension, %R, the difference between the dimension prior to ($\delta_i$) and after subjection to humidity activation ($\delta_f$) needs to be maximized. The present invention provides a method of maximizing the percent recovery, %R, of a given dimension of a material. One factor, which effects the ability to maximize the present recovery of a given dimension, is the ability to "lock-in" a desired amount of shape deformation in the material prior to subjecting the material to humidity.

Preparation of Materials Having a Degree of Shape Deformation

One aspect of the present invention is directed to a method of preparing materials having a desired amount of "locked-in" shape deformation. As used herein, the term "locked-in shape deformation" refers to a recoverable amount of shape deformation in one or more spatial dimensions of a given material, resulting from one or more forces exerted on the given material. Suitable forces include, but are not limited to, stretching, heating, cooling, compressing, bending, coiling, shearing, etc. The amount of locked-in shape deformation may vary depending upon a number of factors including, but not limited to, the material composition, the material temperature, the material treatment procedures (i.e., the amount of stress administered to the material), and any post-treatment procedures (i.e., quenching, tension, etc.). A number of factors, which may contribute to the locked-in shape deformation of a given material are discussed below.

Stretching or Compressing

Stretching and compressing are ways to impart a locked-in shape deformation to a shape deformation material of the present invention. The amount of deformation resulting from stretching or compressing is dependent upon a number of variables. Important variables associated with stretching or compressing of a given material include, but are not limited to, the stretch or draw ratio, the stretching or compressing temperature, the stretching or compressing rate, and post-stretching or post-compressing operations, if any, such as heat setting or annealing operations.

Additionally, other types of deformation may be used besides stretching and compressing including, but not limited to, bending, twisting, shearing, or otherwise shaping the material using complex deformations.

Stretch or Draw Ratio

The amount of locked-in shape deformation that can be imparted to a given material depends upon the stretch or draw ratio. In general, the amount of locked-in shape deformation of a material is typically larger when the draw ratio is larger. Stretching of the material may be accomplished in one or more directions, such as uniaxial or biaxial stretching. Stretching in more than one direction, such as biaxial stretching, may be accomplished simultaneously or sequentially. For example, when sequential biaxial stretching a film of shape deformation material, the first or initial stretching can be conducted in either the machine direction (MD) or the transverse direction (TD) of the film material.

In one embodiment of the present invention, the shape deformation material desirably possesses a draw or stretch ratio of at least 1.5 in one or more directions. More desirably, the material possesses a draw or stretch ratio in one or more directions of from about 2 to about 10. Even more desirably, the material possesses a draw or stretch ratio in one or more directions of from about 3 to about 7. Lower draw ratios may result in low shape deformation and low recoverable deformation. However, low draw ratios may be applicable to some embodiments of the present invention, depending on specific applications and the desired amount of shape deformation. Very high draw ratios during the process of imparting shape-deformation memory may result in a partial loss of shape memory as a result of unrecoverable plastic deformations in the material.

Stretching Temperature

During stretching, the material sample may be optionally heated. Desirably, stretching is conducted at temperatures below the melting temperature of the material. In one embodiment of the present invention wherein the material is a polymeric material, the drawing temperature is not more than about 120° C. and, desirably, not more than about 90° C. When the drawing temperature is too high, the material can melt, become excessively tacky, and/or become difficult to handle. In addition, excessively high stretching temperatures can cause irreversible deformations in which the shape deformation of the material is lost and the original shape is not recoverable.

Stretching a given material at low temperatures may result in a lower amount of locked-in shape deformation and low percent recovery during activation. Generally, when the shape deformation material contains segmented block thermoplastic elastomers, it is desired to stretch the material near the softening or glass transition temperature of the hard segments. In some cases, when the soft segments experience strain induced crystallization during stretching, drawing the material near the crystalline transition temperature of the soft segments is desired. This is the case, for example, when the shape deformation material is a PEBAX® elastomer.

Stretch Rate

The rate at which stretching is performed may also affect the amount of locked-in shape deformation imparted to a given shape deformation material. Suitable stretching rates will vary depending upon the material to be stretched. As a general rule, stretching may be accomplished at rates of at least about 50%/min. and as much as about 5000%/min. Desirably, the stretching rate is from about 100%/min. to about 2500%/min. Higher stretching rates may be more beneficial for process efficiency; however, very high stretching rates may result in a material failure at reduced draw ratios. The effect of stretching rate on locked-in shape deformation is dependent upon the structure and composition of the material. For some embodiments of the present invention, such as when the shape deformation material contains a thermoplastic polyurethane, the stretching rate does not have a significant impact on the resulting amount of locked-in shape deformation.

Post-Stretching Operations

The locked-in shape deformation properties of a shape deformation material of the present invention may be affected by post-stretching operations. A number of factors should be considered during post-stretching operations including, but not limited to, the material composition, the relaxation tendency of the material, and the desired amount of percent recovery for a particular application.

Relaxation Tendency

In most cases, the shape deformation material will possess a tendency to return to its original, pre-stretched configuration. This property may be described as a relaxation tendency. Although the relaxation tendency may vary from material to material, generally, the amount of relaxation tendency increases as the elasticity of the material increases. Further, the amount of relaxation tendency increases for a given material as the temperature of the material increases.

Tension

During post-stretching operations, the stretched material may be held under tension in a stretched state, gradually released from a stretched state over time, or treated in some manner while in a tensionless state. Typically, recoverable shape deformation or percent recovery is larger when the shape deformation material is held in a stretched state for a longer period of time. When the shape deformation material is a polymeric fiber or film, the shape deformation material is desirably held in a stretched state for at least about 30 seconds. More desirably, the shape deformation material is held in a stretched state for at least about ten minutes. Even more desirably, the shape deformation material is held in a stretched state for at least about one hour, and most desirably, about 24 hours. The time under tension depends on a molecular structure of the shape deformation polymer. For poly(ether amide) shape deformation elastomer, e.g. PEBAX® elastomer, the material can be held under tension for a very short period of time. For polyester aromatic and aliphatic polyurethanes with shape deformation, e.g. MORTHANE® polyurethanes, a longer time under tension is preferred. The use of tension, especially in combination with temperature, may be useful to preserve orientation in the shape deformation material and protect the resulting structure against undesirable shrinkage after stretching.

Temperature

The stretched shape deformation material may be subjected to post-stretching operations at room temperature or at elevated temperatures. The "setting" process (i.e., the process of locking-in a desired amount of stretch) may be conducted in accordance with a selected, predetermined temperature-time profile, which is dependent on the structure of the shape deformation material and the relaxation tendency of the shape deformation material. In general, the setting process is conducted at temperatures below the melting temperature of the shape deformation material. Desirably, the setting process is conducted at temperatures above the temperature of secondary relaxation processes and temperatures above the glass transition temperature of the soft segments in segmented block elastomers. This allows the structure to relax during the setting process and reduce relaxation tendency, which can result in increased shape deformation Other Post-Stretching Operations Other additional post-stretching processes or operations, such as UV treatment, ultrasonic treatment, high energy treatment, or combinations of these treatments, may be incorporated into the post-stretching process to enhance the latent deformation by modifying the morphological state of the stretched material and maximizing the percent recovery of the shape deformation material upon activation.

The Activation Process

The present invention is further directed to a method of causing the efficient recovery of at least a portion of the latent, locked-in shape deformation of the above-described shape deformation materials. The method includes subjecting the shape deformation material to an amount of humidity or moisture in order to effect a substantial change (i.e., recovery) in at least one spatial dimension of the material. The method may be used to cause the shape deformation of the above-described shape deformation material itself or a product containing as one or more components the above-described shape deformation material.

Recovery of latent, locked-in shape deformation of the shape deformation material of the present invention is accomplished by exposing the shape deformation material to an environment having at least a 50% relative humidity. Desirably, the humid environment has at least a 75% relative humidity, and more desirably at least a 85% relative humidity.

The shape deformation material of the present invention may be exposed to a sufficient amount of humidity to effect a change in at least one spatial dimension of the material.

Percent recovery may vary depending on a number of factors including, but not limited to, the shape deformation material; the amount of latent, locked-in shape deformation; the pre-activation treatments used to prepare the shape deformation material; and the desired amount of percent recovery for a particular application. For most applications, the percent recovery (%R) is desirably greater than about 30% upon exposure to a humid environment. For most applications, the percent recovery (%R) is more desirably greater than about 60% upon exposure to a humid environment. A preferred range of the percent recovery is from about 15% to about 75% upon exposure to a humid environment.

As discussed above, the use of humidity or moisture in the present invention to activate shape deformation materials is advantageous over conventional methods, which use thermal energy, for a number of reasons. The use of humidity enables rapid molecular reorientation (i.e., recovery) of a shape deformable material having a latent, locked-in amount of shape deformation without a substantial increase in the temperature of the shape deformable material. As used herein, "a substantial increase in the temperature of the shape deformable material" refers to an increase in temperature of greater than about 15° C. Desirably, the shape deformable material exhibits a desired percent recovery while experiencing a temperature change of less than about 12° C.

As opposed to conventional recovery methods, which desire thermal heating of a shape deformable material, the activation process of the present invention desirably minimizes the degree of heating of the shape deformable material. Further, the activation process of the present invention results in no surface overheating of the shape deformation material, reduced material degradation, and energy savings.

In some conventional processes, the recovery of shape deformation is achieved by heating a shape deformable material to temperatures below the melting temperature of the stretched polymer material and above the stretching temperature. Low recovery temperatures may result in low recoverable deformation, while excessively high temperatures may result in melting of the shape-deformed material. However, in the present invention using humidity, the temperature of the environment is not critical. The temperature of the environment surrounding the shape deformable material of the present invention may vary depending on the desired conditions in a given room or the in-use conditions of a garment containing the shape deformable material. For example, the activation process of the present invention may be performed at room temperature or in a cooled or heated zone.

Compared to conventional systems, which have used heated air or heated rolls to activate webs or individual pieces of latent elastic material, the use of humidity during in-use conditions is less expensive. Alternatively, in a manufacturing process for absorbent articles, the entire article may be manufactured and packaged while the shape deformation material of the absorbent article is in a latent state. Prior to shipping the articles, the shape deformation material within the absorbent article may be activated by humidity.

Articles of Manufacture

The present invention is further directed to articles of manufacture, which contain the above-described shape deformable materials. The shape deformable material may represent a substantial part of the article of manufacture or may represent one of many components of the article. Further, the shape deformable material may be used as a single layer component or may be present as one layer of a multi-layer laminate within the article of manufacture. Suitable articles of manufacture include, but are not limited to, products containing an elastic portion, such as diapers, as well as, products having a shrinkable, gatherable or expandable component.

In one embodiment of the present invention, the shape deformable material is in the form of a film, which is laminated to one or more additional layers to form a composite article. The additional layers may include additional films, nonwoven webs, woven fabrics, foams, or a combination thereof. The resulting laminated article is suitable for use in a number of applications, such as disposable absorbent products. Such products include, but are not limited to, absorbent personal care items such as diapers, training pants, adult incontinence products, feminine care products such as sanitary napkins, tampons, and vaginal inserts, and health care products such as wound dressings and delivery systems. Other products include surgical drapes, surgical gowns, and other disposable garments.

The composite material of this embodiment is representatively illustrated in FIG. 1. As can be seen in FIG. 1, the composite material 10 includes a nonwoven web layer 12, and strips of shape deformable material 14 and 16, which are attached to layer 12. The strips of shape deformable material 14 and 16 may be attached to nonwoven web layer 12 by any means known to those of ordinary skill in the art. Depending on the amount and degree of latent, locked-in shape deformation within the strips of shape deformable material 14 and 16, activation of the composite material results in a desired gathered composite material.

Figure 2:
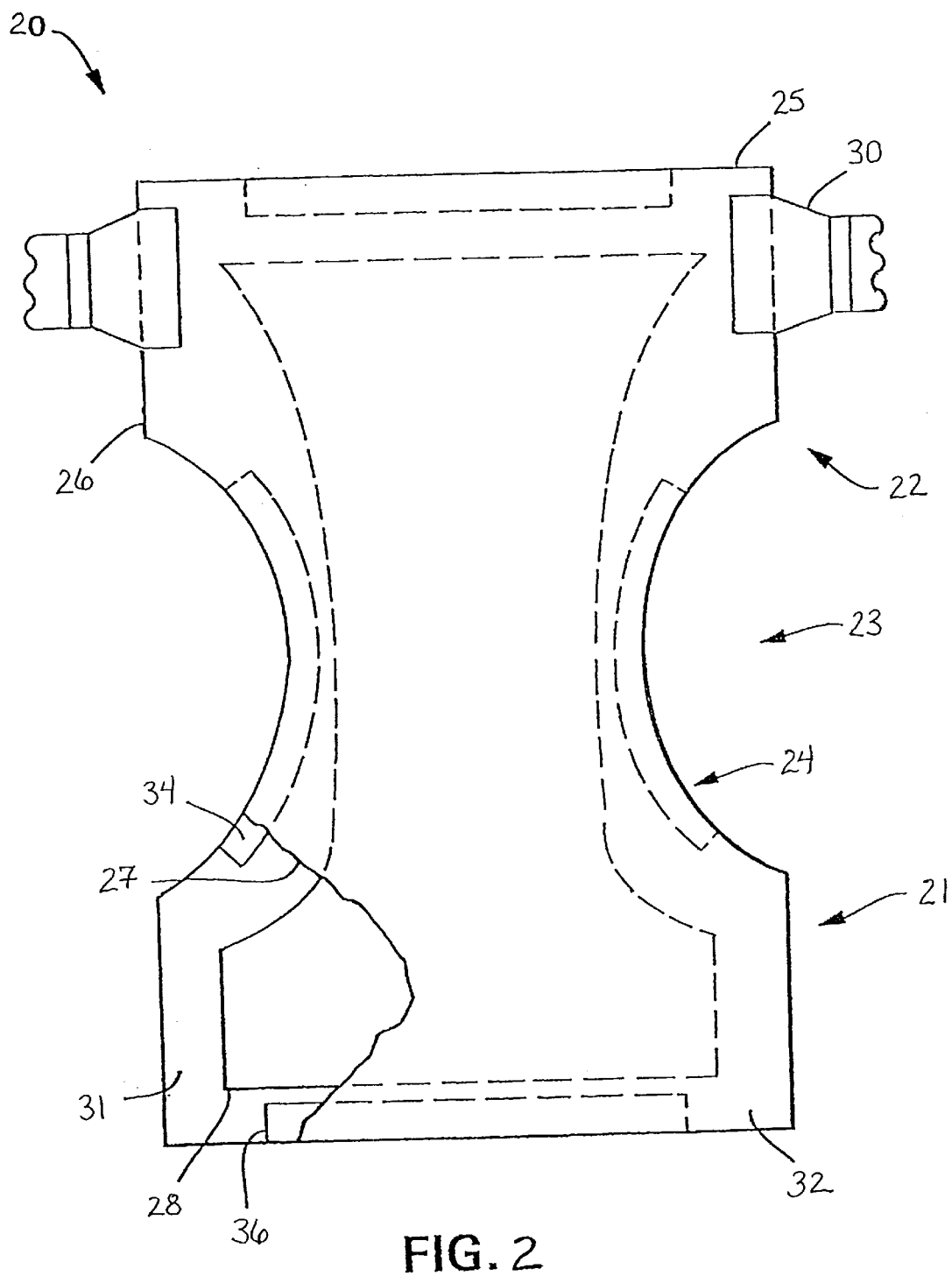
FIG. 2 representatively shows a partially cut away, top plan view of an absorbent article according to one embodiment of the present invention.

One article of manufacture of particular interest is an absorbent garment article representatively illustrated in FIG. 2. As can be seen in FIG. 2, the absorbent garment may be a disposable diaper 20, which includes the following components: a front waist section 21; a rear waist section 22; an intermediate section 23, which interconnects the front and rear waist sections; a pair of laterally opposed side edges 24; and a pair of longitudinally opposed end edges 25. The front and rear waist sections include the general portions of the article, which are constructed to extend substantially over the wearers front and rear abdominal regions, respectively, during use. The intermediate section 23 of the article includes the general portion of the article, which is constructed to extend through the wearer's crotch region between the legs. The opposed side edges 24 define leg openings for the diaper and generally are curvilinear or contoured to more closely fit the legs of the wearer. The opposed end edges 25 define a waist opening for the diaper 20 and typically are straight but may also be curvilinear.

FIG. 2 is a representative plan view of a diaper 20 of the present invention in a flat, uncontracted state. Portions of the structure are partially cut away to more clearly show the interior construction of the diaper 20, and the surface of the diaper which contacts the wearer is facing the viewer. The diaper 20 further includes a substantially liquid impermeable outer cover 26; a porous, liquid permeable bodyside liner 27 positioned in facing relation with the outer cover 26; an absorbent body 28, such as an absorbent pad, which is located between the outer cover and the bodyside liner; and fasteners 30. Marginal portions of the diaper 20, such as marginal sections of the outer cover 26, may extend past the terminal edges of the absorbent body 28. In the illustrated embodiment, for example, the outer cover 26 extends outwardly beyond the terminal marginal edges of the absorbent body 28 to form side margins 31 and end margins 32 of the diaper 20. The bodyside liner 27 is generally coextensive with the outer cover 26, but may optionally cover an area, which is larger or smaller than the area of the outer cover 26, as desired.

Shape deformable material as described above may be incorporated into various parts of the diaper 20 illustrated in FIG. 2. Desirably, a pair of laterally opposed side strips 34 and/or a pair of longitudinally opposed end strips 36 contain the shape deformable material of the present invention. Upon activation, strips 34 and 36 form gathered portions, which provide a snug fit around the waist and leg openings of the diaper 20.

Optimizing Interaction of Polymer with Humidity

The present invention is also directed to a method of making shape deformable polymers in an effort to optimize the interaction of the shape deformable polymer with a selected amount of humidity or moisture. By incorporating one or more selected moieties into the polymer backbone and/or positioning one or more selected moieties at strategic sites along the polymer backbone of the shape deformable polymer, one can tailor a specific shape deformable polymer, which will optimally respond to a selected amount of humidity.

For shape deformable polymers, the efficiency of moisture absorption is related to the permeability and solubility properties of the polymer. Preferably, the shape deformable polymer used in the present invention demonstrates high permeability to water vapor.

As discussed above with regard to functional groups within a shape deformable polymer, specifically selected moieties along the polymer chain and the positioning of moieties along the polymer chain can effect the level of moisture sensitivity of the shape deformable polymer, and enhance the responsiveness of the polymer to humidity. Desirably, the presence of one or more moieties along the polymer chain causes one or more of the following: (1) an increase in the dipole moments of the polymer; and (2) an increase in the unbalanced charges of the polymer molecular structure. Suitable moieties include, but are not limited to, aldehyde, urea, amide, nitro, nitrile, ester, ether, hydroxyl, ethylene oxide, amine, carboxylic acid, and sulfonamide groups, carboxylic acid salts and sulfonic acid salts.

The selected moieties may be covalently bonded or ionically attached to the polymer chain. As discussed above, moieties containing functional groups having high dipole moments are desired along the polymer chain. Suitable moieties include, but are not limited to, urea, amide, nitro, and nitrile groups. Other suitable moieties include moieties containing ionic groups including, but are not limited to, sodium, zinc, and potassium ions.

One example of modifying a polymer chain to enhance the responsiveness of the polymer chain is shown below:

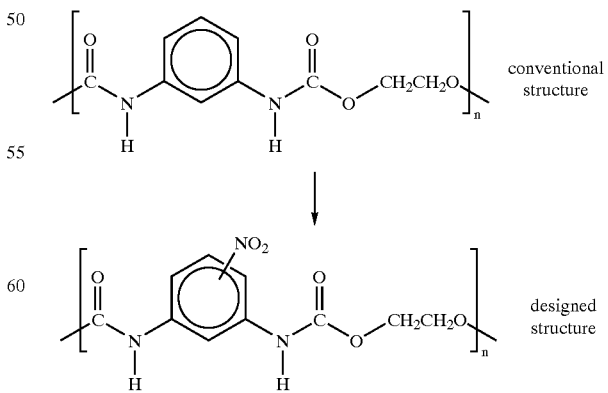

In the above example, a nitro group is attached to the aryl group within the polymer chain. It should be noted that the nitro group may be attached at the meta or para position of the aryl group. Further, it should be noted that other groups may be attached at the meta or para position of the aryl group, as shown above, in place of the nitro group. Suitable groups include, but are not limited to, nitrile groups. In addition to the modification shown above, one could incorporate other monomer units into the polymer above to further enhance the responsiveness of the resulting polymer. For example, monomer units containing ethylene oxide, urea and/or amide groups may be incorporated into the above polymer.

In another example, polyether-type thermoplastic polyurethane with a shape memory can contain soft blocks comprising polyethylene oxide (PEO) blocks or segments. The molecular weight of the polyethylene oxide segments within the polyurethane can vary from about 1000 to about 100,000. Preferably the polyethylene oxide blocks or segments can crystallize to form crystals in an ambient environment. Crystallizable PEO blocks or segments can enhance shape memory properties and increase response to humidity.

A further example of designing a shape deformable polymer is given below, wherein one or more moieties, X and Y, are bonded to specific sites along a block copolymer chain:

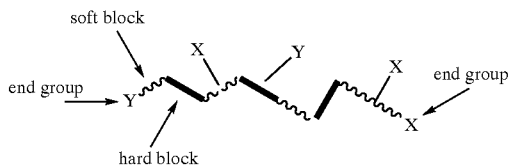

X and Y may be bonded to or otherwise incorporated in soft blocks, hard blocks, or both soft and hard blocks, as well as, on the ends of the polymer chain. X and Y may be randomly bonded or uniformly bonded along the polymer chain. Suitable moieties include aldehyde, ethylene oxide, ester, carboxylic acid, and sulfonamide groups. However, other groups having or enhancing unbalanced charges in a molecular structure can also be useful; or a moiety having an ionic or conductive group such as, e.g., sodium, zinc, and potassium ions. However, other ionic or conductive groups can also be used.

It should be noted that moieties X and Y may also be bonded to or otherwise incorporated into the same soft or hard block within a given polymer chain. In one embodiment shown below, X and Y are bonded to the same soft or hard block within a given polymer, wherein X is a moiety having a positive charge and Y is a moiety having a negative charge:

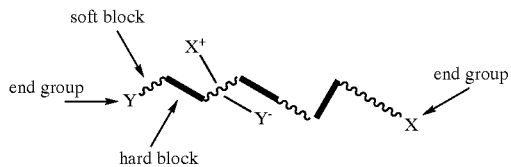

In such a configuration, the unbalanced charge within one polymer segment results in enhanced interaction between the polymer and humidity, or between the polymer and a humidity sensitive component.

EXAMPLES

The following examples were conducted to produce shape deformation materials having an amount of locked-in shape deformation, and to activate the materials. Degree of stretch/stretch ratio, stretch rate, and stretch hold/cooling rate were some of the factors considered in order to introduce the most latent, lock-in shape deformation.

Examples 1–6 demonstrate activation of shape deformation material using humidity.

Example 1

A multilayer film of eight alternating layers of MORTHANE® polyurethane (PU) PS370-200 and polyethylene oxide (PEO) resin was produced using a microlayer coextrusion line available at Case Western Reserve University, Cleveland, Ohio. The PEO resin POLYOX® WSR-N-3000 was supplied by Union Carbide Corporation in a powder form and pelletized at Planet Polymer Technologies of San Diego, Calif. Rectangular strips of multilayer PU PS370-200/PEO (50/50) film were stretched to six times their original length at 25° C. using a Sintech tensile tester. The resulting latent deformation was about 340% in film length. The stretched film sample was placed in an environmental oven held at a temperature of 37° C. and 80% relative humidity. After 20 minutes in the environmental oven the sample was removed and dimensions were measured. The dimensional change of the film in machine direction was 32% as compared to the stretched-film length.

Example 2

The multilayer film of Example 1 was stretched to six times at 25° C. using a SINTECH tensile tester. The resulting latent deformation was about 350% in length. The stretched film sample was placed in an environmental oven held at a temperature of 37° C. and 95% relative humidity. After 20 minutes in the environmental oven, the sample was removed and dimensions were measured. The dimensional change of the film in machine direction was 66% as compared to the stretched-film length.

Example 3

A 50/50 blend of MORTHANE® polyurethane (PU) PS370-200 and PEO was produced using the Haake laboratory twin screw extruder. The rectangular strips of film made of 50/50 blend were stretched to six times at 25° C. The resulting latent deformation was about 185% in length. The stretched sample was placed in an environmental oven held at a temperature of 37° C. and 95% relative humidity. After 20 minutes in the environmental oven the sample was removed and dimensions were measured. The dimensional change of the film in machine direction was 53% as compared to the stretched-film length.

Example 4

A microlayer film of 256 alternating layers of PU PS370-200 and PEO resin was produced using a microlayer coextrusion line available at Case Western Reserve University, Cleveland, Ohio. The rectangular strips of multilayer PU PS370-200/PEO (70/30) film were stretched to six times at 25° C. using a Sintech tensile tester. The resulting latent deformation was about 150% in film length. The stretched film sample was placed in an environmental oven held at a temperature of 37° C. and 95% relative humidity. After 20 minutes in the environmental oven, the sample was removed and the dimensions of the film were measured. The dimensional change of the film in machine direction was 46% as compared to the stretched-film length.

Example 5

A microlayer film was produced using the method in Example 4, except a 16 layer PU/PEO (70/30) film was developed. The film was stretched to produce a latent deformation of 180% in length. The stretched film sample was placed in an environmental oven and held at a temperature of 37° C. and 80% relative humidity. After 20 minutes in an environmental oven, the sample was removed and the dimensions of the film were measured. The dimensional change of the film in machine direction was 50%.

Example 6

A 70/30 blend of MORTHANE® polyurethane (PU) PS370-200 and PEO was produced using the Haake laboratory twin screw extruder. The rectangular strips of film made of 70/30 blend were stretched to six times at 25° C. The resulting latent deformation was about 100% in length. The stretched sample was placed in an environmental oven held at a temperature of 37° C. and 80% relative humidity. After 20 minutes in the environmental oven the sample was removed and the dimensions of the film were measured. The dimensional change of the film in machine direction was 30% as compared to the stretched-film length.

Comparative Example 1
Activation of Sample Using Thermal Energy

The multi-layer PU PS370-200/PEO (50/50) film of Example 1 was stretched to 6 times its original length at 25° C. using a Sintech tensile tester. The resulting latent deformation was about 330%. The stretched sample was placed in a convection oven for 20 minutes at a temperature of 73° C. The sample was removed from the oven, and its dimensions were measured. The dimensional change of the film in the MD was 65% based on the stretched film length.

Comparative Example 2
Activation of Sample Using Thermal Energy

A 50/50 blend of PU PS370-200 and polyethylene oxide (PEO) was produced using a Haake laboratory twin screw extruder. Rectangular strips of film, made from the 50/50 blend, were stretched to 6 times their original length at 25° C. The resulting latent deformation was about 170%. The stretched sample was placed in a convection oven for 20 minutes at a temperature of 65° C. The sample was removed from the oven, and its dimensions were measured. The dimensional change of the film in the MD was 63% based on the stretched film length.

Examples 7–10 demonstrate the effect of stretch rate, draw ratio, stretch temperature, stretch hold and cooling rate on the amount of locked-in shape deformation.

Stretching Procedures to Impart Latent Deformation

An MTS Sintech 1/D instrument equipped with a 50-pound load cell and an environmental chamber was used to stretch the samples to impart a desired amount of shape deformation. Samples of each film were cut 1" wide by 3" to 4" long and were labeled and marked in black ink with lines 20 mm apart. Samples were then placed in the grips of the MTS Sintech 1/D instrument spaced 2" apart and stretched a desired amount. Samples were stretched from 3× (i.e., three times the original length) to more than 6×, at a desired stretch rate. Stretch rates were either 100 mm/min (i.e., the "slow" rate) or 500 mm/min (i.e., the "fast" rate). When necessary, the grips and sample were placed in the environmental chamber and heated to a desired temperature, which varied from about 37° C. to about 100° C., allowed to equilibrate, and then stretched the desired amount at the desired rate.

Unless otherwise noted, after stretching, the sample was held stretched at the stretching temperature for 1 minute. Then, the sample was cooled by one of two methods. "Slow cooling" was one method wherein the environmental chamber door was opened and the stretched sample exposed to a fan until the sample had reached room temperature at which point the sample was released from the stretched position and removed. The other method was "quenching," wherein the environmental chamber door was opened and the sample was sprayed with a cooling agent (i.e., Blow-Off freeze spray comprising 1,1,1,2-tetrafluoroethane) for a number of passes while the sample was released from the stretched position and removed from the chamber.

The distance between the lines was measured and recorded and new lines were marked in red 20 mm or 40 mm apart depending upon the sample length. Latent, locked-in shape deformation, or percent latency, was defined as the change in length from the stretched sample to the initial sample, divided by the initial sample length, and multiplied by 100.

Example 7
Effect of Stretch Rate on the Amount of Locked-in Shape Deformation

Rectangular strips of MORTHANE® PS370-200 were stretched using a slow stretch rate and a fast stretch rate. The strips were stretched up to 6 times their initial length at three separate temperatures, 25° C., 50° C., and 70° C. using a Sintech tensile tester (SINTECH 1/D) and an environmental chamber.

The results of the tests are given below in Table 1.

TABLE 1

| | Stretch Rate Results | | | | | |
|---|---|---|---|---|---|---|
| Temperature | 25° C. | | 50° C. | | 70° C. | |
| Stretch Rate | Slow | Fast | Slow | Fast | Slow | Fast |
| % Latency | 15 | 20 | 75 | 75 | 145 | 150 |

As can be seen in Table 1, the stretch rate did not significantly effect the percent latency of MORTHANE® PS370-200. However, the temperature had a significantly effect on the percent latency of MORTHANE® PS370-200.

Example 8
Effect of Draw Ratio on the Amount of Locked-in Shape Deformation

Rectangular strips of MORTHANE® PS370-200 were stretched using three different draw ratios: 4×, 5×, and 6×. The strips were stretched at three separate temperatures, 25° C., 50° C., and 70° C. using a Sintech tensile tester (SINTECH 1/D) and an environmental chamber.

The results of the tests are given below in Table 2.

TABLE 2

| | Draw Ratio Results | | | | | | | | |
|---|---|---|---|---|---|---|---|---|---|
| Temperature | 25° C. | | | 50° C. | | | 70° C. | | |
| Draw Ratio | 4× | 5× | 6× | 4× | 5× | 6× | 4× | 5× | 6× |
| % Latency | 15 | 15 | 25 | 80 | 120 | 75 | 125 | — | 150 |

As can be seen in Table 2, the draw ratio did not significantly effect the percent latency of MORTHANE® PS370-200.

Example 9
Effect of Stretch Temperature on the Amount of Locked-in Shape Deformation Rectangular strips of MORTHANE® PS370-200 were stretched using three different temperatures: 25° C., 50° C., and 70° C. The strips were stretched at two different draw ratios, 4× and 6×, using a Sintech tensile tester (SINTECH 1/D) and an environmental chamber.

The results of the tests are given below in Table 3.

TABLE 3

| | Temperature Results | | | | | |
|---|---|---|---|---|---|---|
| Temperature | 25° C. | | 50° C. | | 70° C. | |
| Draw Ratio | 4× | 6× | 4× | 6× | 4× | 6× |
| % Latency | 15 | 25 | 80 | — | 125 | 150 |

As can be seen in Table 3, the stretch temperature had a significant effect on the percent latency of MORTHANE® PS370-200.

Example 10
Effect of Stretch Hold and Cooling Rate on the Amount of Locked-in Shape Deformation Rectangular strips of MORTHANE® PS370-200 were stretched at different temperatures: 70° C. and 90° C. The strips were stretched at a draw ratio of 6×, using a Sintech tensile tester (SINTECH 1/D) and an environmental chamber. The samples were either slowly cooled or quenched as described above. The samples were allowed to cool or quenched after being held in a stretched position for one minute, and also without being held.

The results of the tests are given below in Table 4.

TABLE 4

| | Stretch Hold/Cooling Rate Results | | | | | | | |
|---|---|---|---|---|---|---|---|---|
| Temperature | 70° C. | | | | 90° C. | | | |
| Stretch Hold | Load | | No Load | | Load | | No Load | |
| Cooling Method | SC | Q | SC | Q | SC | Q | SC | Q |
| % Latency | 145 | 145 | 140 | 150 | 235 | 180 | 210 | 190 |

As can be seen in Table 4, the MORTHANE® PS370-200 samples had a larger amount of percent latency when slowly cooled after being held for one minute at a given stretch temperature and then allowed to cool as opposed to the samples allowed to cool without being held. Quenching reduced the amount of time the samples were held and allowed to relax. Consequently, these samples generally had less percent latency. However, conclusions regarding the overall effect of quenching was hard to determine from the above data.

The results of the MORTHANE® PS370-200 samples at 90° C. indicate that stretch holding and cooling rate has a more significant effect on the percent latency than similar samples tested at 70° C. In these samples, slow cooling produced the best results in percent latency.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of preparing a humidity responsive material having shape memory, wherein the process comprises:
    forming a humidity responsive material comprising a shape deformable matrix material comprising an elastomeric polymer and a non-elastomeric polymer;
    forming a latent deformation in the humidity responsive material, wherein the humidity responsive material is capable of being deformed in at least one spatial dimension when exposed to one or more external forces, is capable of maintaining a degree of deformation in at least one spatial dimension once the external force is removed, and is capable of exhibiting a change, or percent recovery, in at least one spatial dimension when subjected to a humid environment;
    wherein the percent recovery is greater than about 60% when subjected to a humid environment;
    wherein the humid environment has a relative humidity of at least 50%;
    wherein the humidity responsive material exhibits a temperature change of less than about 15° C. when subjected to the humid environment.

2. The method of claim 1, wherein the latent deformation is formed by stretching the humidity responsive material.

3. The method of claim 2, wherein the stretched material possesses a draw or stretch ratio of at least 1.5 in one or more directions.

4. The method of claim 2, wherein the stretched material possesses a draw or stretch ratio in one or more directions of from about 2 to about 10.

5. The method of claim 2, wherein the stretched material possesses a draw or stretch ratio in one or more directions of from about 3 to about 7.

6. The method of claim 2, wherein the humidity responsive material is heated during stretching to a temperature of not more than about 120° C.

7. The method of claim 2, wherein the humidity responsive material is heated during stretching to a temperature of not more than about 90° C.

8. The method of claim 2, wherein the stretching is accomplished at a rate of between about 50%/min. to about 5000%/min.

9. The method of claim 2, wherein the stretching is accomplished at a rate of between about 100%/min. to about 2500%/min.

10. The method of claim 1, wherein the shape deformable matrix material comprises polyester-based thermoplastic polyurethane; polyether-based polyurethane; polyethylene oxide; poly(ether ester) block copolymer; polyamide; poly(amide ester); poly(ether amide) copolymer; polyvinyl alcohol; polyvinyl pyrolidone; polyvinyl pyridine; polyacrylic acid; polymethacrylic acid; polyaspartic acid; maleic anhydride methylvinyl ether copolymers; polyvinyl methyl ether copolymers of polyacrylic acid and polyacrylic ester; segmented block copolymer having one or more hard segments and one or more soft segments; or mixtures thereof.

11. The method of claim 1, wherein the shape deformable matrix material comprises a multi-layer or micro-layer structure having separate layers of an elastomeric polymer and a non-elastomeric polymer.

12. The method of claim 1, wherein the shape deformable matrix material comprises an elastomeric polymer; and a moisture absorbing polymer, wherein the moisture absorbing polymer exhibits at least a 20% reduction in modulus when the material is exposed to a humid environment.

13. The method of claim 12, wherein the moisture absorbing polymer exhibits at least a 30% reduction in modulus when the material is exposed to a humid environment.

14. The method of claim 12, wherein the moisture absorbing polymer exhibits at least a 50% reduction in modulus when the material is exposed to a humid environment.

15. The method of claim 12, wherein the elastomeric polymer comprises thermoplastic polyurethane, poly(ether-amide) block copolymer, styrene-butadiene copolymer, silicon rubber, styrene isoprene copolymer, styrene ethylene butylene copolymer, butyl rubber, nylon copolymer, spandex fibers comprising segmented polyurethane, ethylene-vinyl acetate copolymer or mixtures thereof.

16. The method of claim 12, wherein the moisture absorbing polymer comprises polyethylene oxide, polyethylene glycol, polyvinyl alcohol, polyvinyl pyrolidone, polyvinyl pyridine, or mixtures thereof.

17. The method of claim 12, wherein the shape deformable matrix material comprises from about 5% to about 90% by weight moisture absorbing polymer.

18. The method of claim 12, wherein the shape deformable matrix material comprises from about 10% to about 60% by weight moisture absorbing polymer.

19. The method of claim 12, wherein the shape deformable matrix material comprises from about 10% to about 95% by weight elastomeric polymer.

20. The method of claim 12, wherein the shape deformable matrix material comprises from about 50% to about 70% by weight elastomeric polymer.

21. The method of claim 1, further comprising the step of treating the material to enhance the latent deformation.

22. The method of claim 21, wherein the step of treating the humidity responsive material to enhance the latent deformation is selected from UV treatment, ultrasonic treatment, high energy treatment, or combinations of these treatments.

23. The method of claim 1, wherein the humid environment has a relative humidity of at least 75%.

24. The method of claim 1, wherein the humid environment has a relative humidity of at least 85%.

25. The method of claim 1, wherein the humidity responsive material exhibits a temperature change of less than about 12° C. when subjected to the humid environment.

26. The method of claim 1, wherein the humidity responsive material exhibits at least a 20% reduction in modulus when the material is exposed to a humid environment.

27. The method of claim 1, wherein the humidity responsive material exhibits at least a 30% reduction in modulus when the material is exposed to a humid environment.

28. The method of claim 1, wherein the humidity responsive material exhibits at least a 50% reduction in modulus when the material is exposed to a humid environment.

29. The method of claim 12, wherein the elastomeric polymer comprises thermoplastic rubber, synthetic rubber, or mixtures thereof.

* * * * *